(12) United States Patent
Bonney et al.

(10) Patent No.: US 7,454,267 B2
(45) Date of Patent: *Nov. 18, 2008

(54) MEDICAMENT DISPENSER

(75) Inventors: Stanley George Bonney, Ware (GB);
Anthony Patrick Jones, Ware (GB);
Duncan Robertson, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/427,886

(22) Filed: Jun. 30, 2006

(65) Prior Publication Data

US 2006/0237002 A1  Oct. 26, 2006

Related U.S. Application Data

(63) Continuation of application No. 10/473,902, filed as application No. PCT/GB02/01558 on Apr. 2, 2002, now Pat. No. 7,072,738.

(30) Foreign Application Priority Data

Apr. 2, 2001 (GB) ................... 0108228.8

(51) Int. Cl.
*G06F 17/00* (2006.01)
(52) U.S. Cl. .............. 700/237; 700/231; 700/232; 700/236; 700/242; 700/244; 221/2
(58) Field of Classification Search ......... 221/1–312 C; 700/231–244
See application file for complete search history.

(56) References Cited

U.S. PATENT DOCUMENTS

| | | | |
|---|---|---|---|
| 4,785,969 A | 11/1988 | McLaughlin | |
| 4,857,713 A | 8/1989 | Brown | |
| 5,338,157 A | 8/1994 | Blomquist | |
| 5,401,059 A | 3/1995 | Ferrario | |
| 5,408,443 A | 4/1995 | Weinberger | |

(Continued)

FOREIGN PATENT DOCUMENTS

DE 19852602 5/2000

(Continued)

OTHER PUBLICATIONS

U.S. Appl. No. 10/473,918, filed on Feb. 23, 2004.

(Continued)

*Primary Examiner*—Gene O. Crawford
*Assistant Examiner*—Michael K Collins
(74) *Attorney, Agent, or Firm*—James P. Riek

(57) ABSTRACT

A method of controlling the functioning of a portable medicament dispenser, said portable medicament dispenser being for use with a refill container, said method comprising: (a) providing a memory for storing one or more parameters relating to the functioning of said dispenser; (b) storing authentication data for authenticating data for controlling a function of said dispenser; (c) receiving control data for said dispenser; (d) performing authentication of the control data using said stored authentication data; (e) in dependence on a result of the authentication, activating one or more parameters in said memory to control functioning of said dispenser in accordance with said control data, characterized in that the step (d) of performing authentication of the control data is performed by said refill container.

28 Claims, 11 Drawing Sheets

U.S. PATENT DOCUMENTS

| | | |
|---|---|---|
| 5,703,786 A | 12/1997 | Conkright |
| 5,711,297 A | 1/1998 | Iliff |
| 5,772,586 A | 6/1998 | Heinonen et al. |
| 5,850,344 A | 12/1998 | Conkright |
| 5,924,074 A | 7/1999 | Evans |
| 5,950,630 A | 9/1999 | Portwood |
| 5,960,403 A | 9/1999 | Brown |
| 5,963,136 A | 10/1999 | O'Brien |
| 5,995,938 A | 11/1999 | Whaley |
| 6,000,828 A | 12/1999 | Leet |
| 6,004,020 A | 12/1999 | Bartur |
| 6,021,392 A | 2/2000 | Lester et al. |
| 6,032,155 A | 2/2000 | De La Huerga |
| 6,047,259 A | 4/2000 | Campbell et al. |
| 6,055,494 A | 4/2000 | Friedman |
| 6,055,507 A | 4/2000 | Cunningham |
| 6,119,892 A | 9/2000 | Laurent et al. |
| 6,135,949 A | 10/2000 | Russo et al. |
| 6,148,815 A | 11/2000 | Wolf |
| 6,202,642 B1 | 3/2001 | McKinnon et al. |
| 6,206,590 B1 | 3/2001 | Thomas et al. |
| 6,231,519 B1 | 5/2001 | Blants et al. |
| 6,294,999 B1 | 9/2001 | Yarin et al. |
| 6,540,672 B1 | 4/2003 | Simonsen et al. |
| 6,611,733 B1 | 8/2003 | De La Huerga |
| 6,611,806 B1 | 8/2003 | Harvey |
| 6,625,518 B2 | 9/2003 | Depeursinge |
| 6,656,114 B1 | 12/2003 | Poulsen et al. |
| 6,702,146 B2 | 3/2004 | Varis |
| 7,072,738 B2 * | 7/2006 | Bonney et al. ............... 700/237 |
| 2004/0039255 A1 | 2/2004 | Simonsen et al. |
| 2004/0215490 A1 | 10/2004 | Duchon et al. |

FOREIGN PATENT DOCUMENTS

| | | |
|---|---|---|
| EP | 999506 | 5/2000 |
| WO | WO 99/10830 | 3/1999 |
| WO | WO 99/35588 | 7/1999 |
| WO | WO 00/14652 | 3/2000 |
| WO | WO 00/32098 | 8/2000 |
| WO | WO 00/32258 | 8/2000 |
| WO | WO 00/58901 | 10/2000 |
| WO | WO 00/60449 | 10/2000 |
| WO | WO 00/60522 | 10/2000 |
| WO | WO 00/62221 | 10/2000 |
| WO | WO 00/65522 | 11/2000 |
| WO | WO 00/65996 | 11/2000 |
| WO | WO 00/67173 | 11/2000 |
| WO | WO 00/67185 | 11/2000 |
| WO | WO 00/70889 | 11/2000 |
| WO | WO 01/08106 | 2/2001 |
| WO | WO 02/17850 | 3/2002 |

OTHER PUBLICATIONS

U.S. Appl. No. 10/473,897, filed on Mar. 30, 2004.
U.S. Appl. No. 10/473,899, filed on Jan. 5, 2005.

* cited by examiner

| DISPENSER ID | FIELD #1 | ... | PATIENT ID |
|---|---|---|---|
| _____ | – | – | _____ |
| _____ | – | – | _____ |
| ... | ... | ... | ... |

FIG. 3

| REFILL ID | FIELD #1 | ... | PATIENT ID |
|---|---|---|---|
| _____ | – | – | _____ |
| _____ | – | – | _____ |
| ... | ... | ... | ... |

FIG. 4

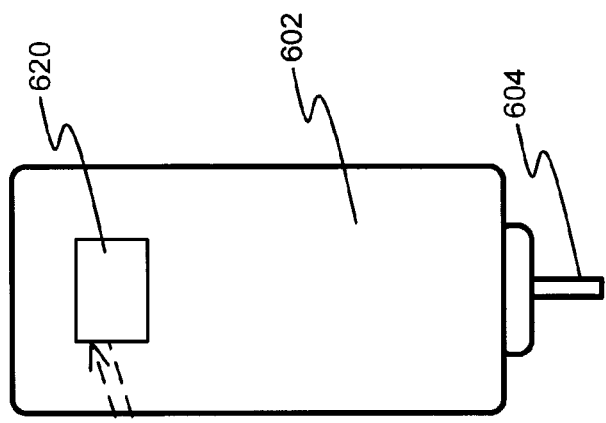
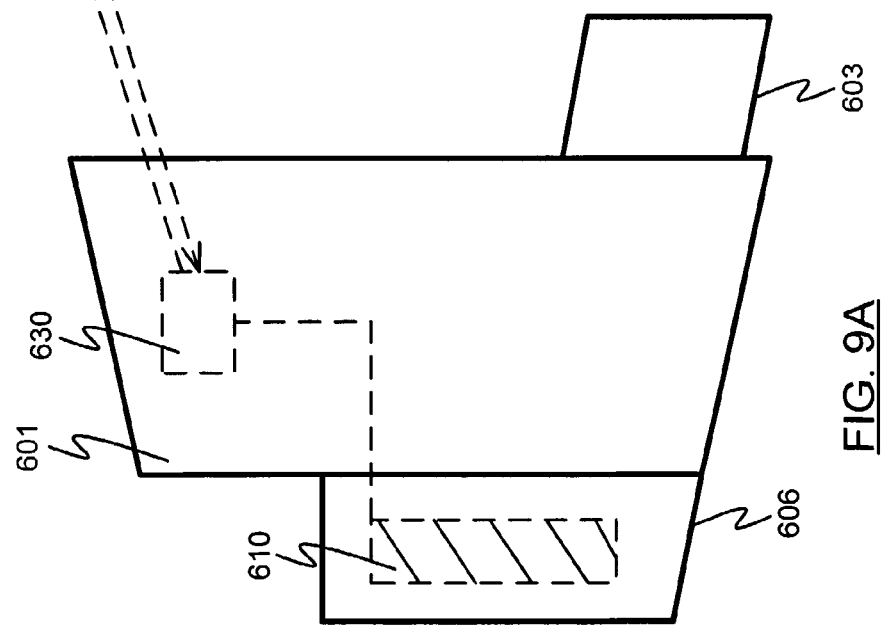

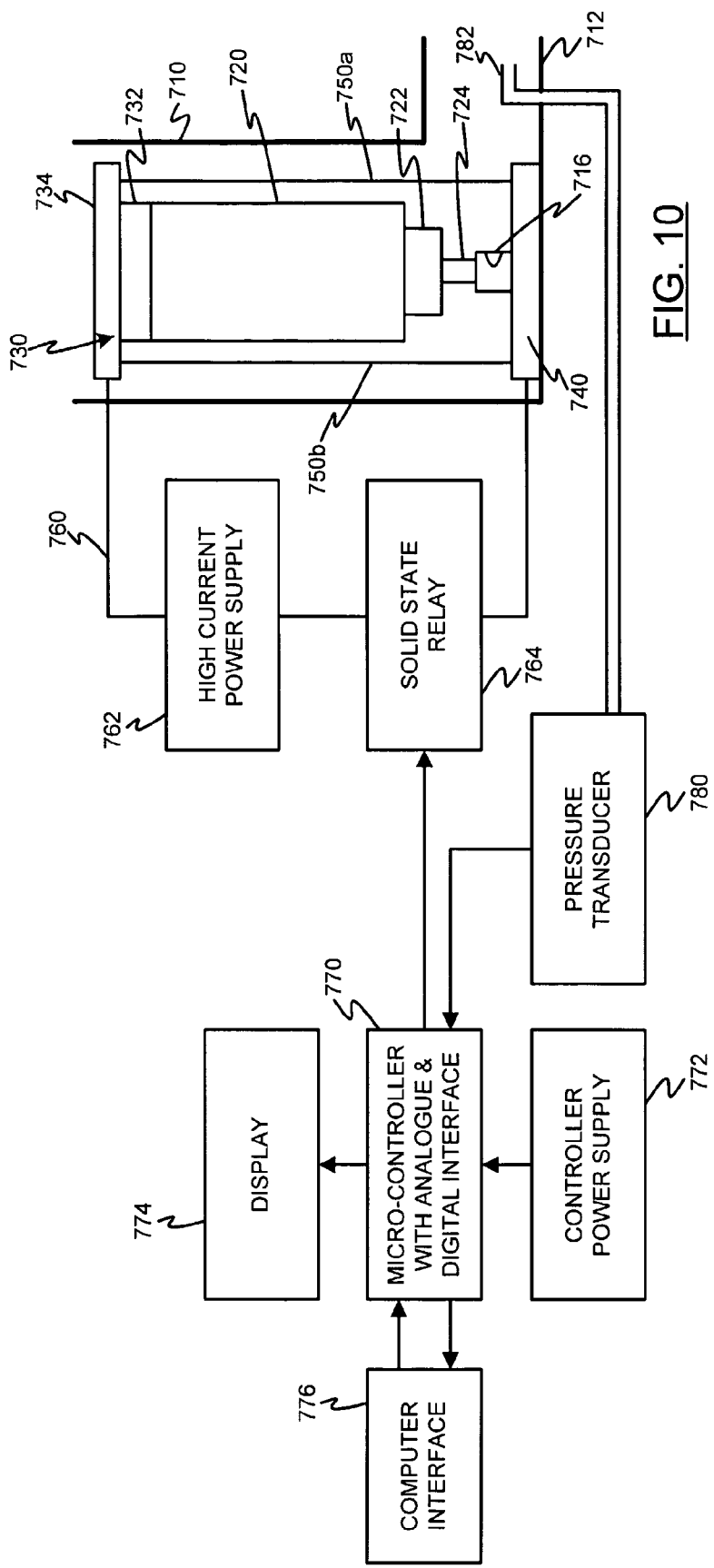

MEDICAMENT DISPENSER

This application is a Continuation of U.S. Pat. application Ser. No. 10/473,902 filed 21 Apr. 2004, now allowed, which was filed pursuant to 35 USC 371 as a United States National Phase Application of International Patent Application Serial No. PCT/GB/02/01558 filed 2 Apr. 2002, which claims priority from GB 0108228.8 filed on 02 Apr. 2001 in the United Kingdom.

The present invention relates to medicament dispensers for use in the dispensing of medicament, to medicament containers for use in same, and to systems and methods for the dispensing of medicament.

Lack of patient compliance with medical treatment regimens is known to be a problem. According to the United States Food and Drug Administration (FDA), between 30 and 50 percent of patients fail to use medicines as prescribed, see "FDA Proposes Program to Give Patients Better Medication Information". The main problems are known to be taking improper dose, failing to take doses on time and ceasing treatment prematurely. If this problem could be addressed, the quality of care offered to patients could be improved considerably.

Medical dispensers are well known for the dispensing of various kinds of medicament. In their most simple form, they may comprise a container of tablets with a removable lid or blister packs of tablets. Inhalation devices, such as metered dose inhalers (MDI) and dry powder inhalers are known for the delivery of medicament for the treatment of respiratory disorders. Syringes, including needleless syringes are also known for the delivery of injectable medicament to a patient.

Reloadable medicament dispensers are known. These typically comprise a housing defining a cavity and a medicament container, referred to herein as a refill, which is reversibly receivable thereby. The housing and the medicament container may be sold separately or as a kit of parts.

Currently, medicament dispensers are primarily manually operable. A patient actuates the dispenser in order to receive a dose of the medicament. If a variation in the basic dose, e.g. more than one dose, is required, the patient typically manually administers two doses. It would be desirable to provide a way in which the patient is relieved of sole responsibility for the correct administration of doses of medicament, and more preferably the variation of such doses, within a treatment regimen.

Further desirable features relating to medicament dispensers include ease of use, portability and ease of manufacture.

PCT patent application no. WO92/17231 describes a metered dose inhaler having a microelectronic assembly thereon. The medicament container includes a set of electrically conducting strips which represent information about the medicament container in digital form. The housing of the device includes electrical contact fingers which are contactable with the strips to enable reading of the information to a microelectronic memory on the housing. Read/write communication would not be possible between the fingers and the reader and the significant advantages of the present invention would therefore not be achievable with this inhaler. Furthermore, contact between the strips on the container and the electrical contact fingers is required which requires physical tailoring of the container to the housing, thereby limiting product design options. This document also describes an embodiment in which an active (i.e. powered) microelectronic element is attached to the container.

PCT Patent Application No. WO 00/25720 describes a medication container that organises several vials or cassettes of different types of medication by securing the vials to a unitary lid. A machine readable memory strip is affixed to each vial. Each memory contains prescription information and medication implementation pertaining to the medication in the vial. The unitary lid is equipped with sensors that read each memory strip and transmit the information to a processor in the lid. The processor determines when each medication is to be taken and signals the patient to take the appropriate medication from the appropriate vial at the appropriate time. The automated lid also contains a receiver for obtaining updated medication dosing information based on current laboratory tests or physical observations of the physician regarding the patient.

One problem with using an automated device which aids patient compliance with medical treatment regimens is that, if the device is closely tied to the dispensing system, the type of information and reminders that may be provided includes that which is typically regarded as needing to be given by a qualified expert, such as a physician or pharmacist. Assumption of responsibility for such tasks by an automated device leads to the possibility of incorrect information being provided to a user, thereby exposing the user to potential risk, in the case of information or reminders being given remote from a qualified expert. It is an object of the present invention to overcome this drawback.

In accordance with one aspect of the present invention there is provided a method of controlling the functioning of a portable medicament dispenser, said method comprising:

(a) providing a memory for storing one or more parameters relating to the functioning of said dispenser;

(b) storing authentication data for authenticating data for controlling a function of said dispenser;

(c) receiving control data for said dispenser;

(d) performing authentication of the control data using said stored authentication data;

(e) in dependence on a result of the authentication, activating one or more parameters in said memory to control functioning of said dispenser in accordance with said control data.

In accordance with a further aspect of the invention there is provided a method of controlling the functioning of a portable medicament dispenser, said method comprising:

(a) providing a network node connected to a communications network, said node having access to a database for storing one or more parameters relating to the functioning of said dispenser;

(b) generating control data for said dispenser using said one or more parameters; and (c) generating authentication data based on said control data to produce authenticatable control data;

(d) arranging for said authenticatable control data to be transmitted to said dispenser, so as to allow said dispenser to authenticate the generated control data.

By performing authentication of control data used for controlling the functioning of a portable medicament dispenser, and in dependence on the result of the authentication, activating parameters in the memory to control function of the dispenser, the functioning of the dispenser can be maintained within the control of a qualified expert whilst allowing the control data to be input into a dispenser without requiring the presence of such an expert.

In one embodiment, the portable medicament dispenser is for use with a refill container, and the control data comprises control data received from such a refill container. In this case, the refill container may be dispensed by a registered pharmacist having access to authenticable refill containers, whilst the control data may be input into, and authenticated by, a medicament dispenser after dispensing, when the refill container is first placed in a medicament dispenser for use.

In a further embodiment of the invention, the portable medicament dispenser is for use with a node of a data communications network, and the control data comprises control data received from said network node. In this case, a qualified expert, such as a physician, may update data, using a secure access procedure, on the network node, and then corresponding authenticable control data may be delivered via a remote communications link.

Further features and advantages of the present invention will become apparent from the following description of preferred embodiments of the invention.

Embodiments arranged in accordance with the invention will now be described, by way of example only, with reference to the accompanying drawings in which:

FIGS. 3 and 4 illustrate look-up tables used in embodiments of the invention;

FIGS. 8 to 11 illustrate embodiments of patient apparatus in greater detail.

FIG. 1 illustrates a healthcare management system arranged in accordance with an embodiment of the invention. The system includes a patient healthcare management system A, a healthcare service provider data management system B, a physician's data management system C, a pharmacy data management system D, and manufacturer data management system E.

Figure 1A:
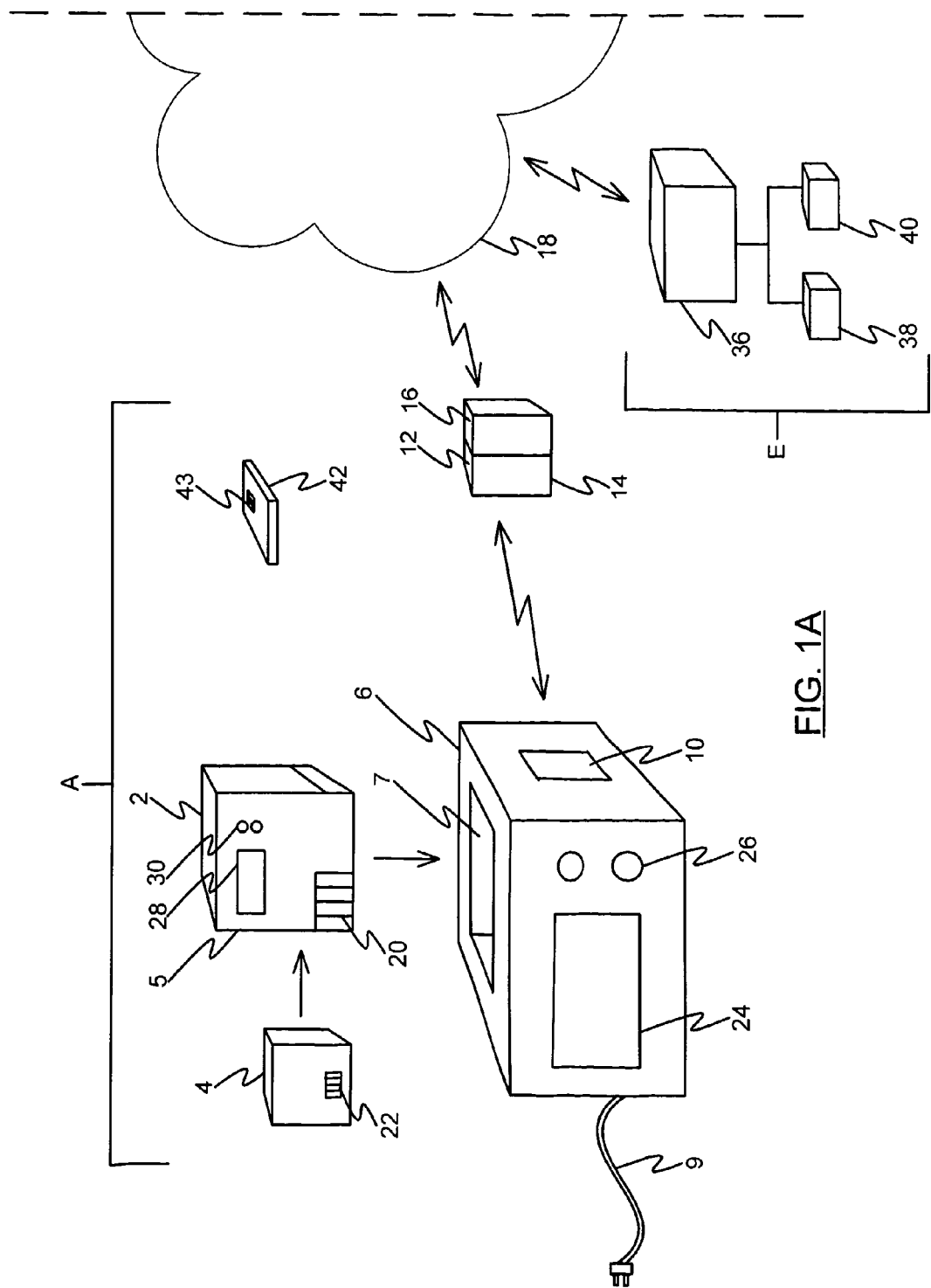
FIG. 1 is a schematic illustration of a healthcare management system in accordance with an embodiment of the invention.
Figure 1B:
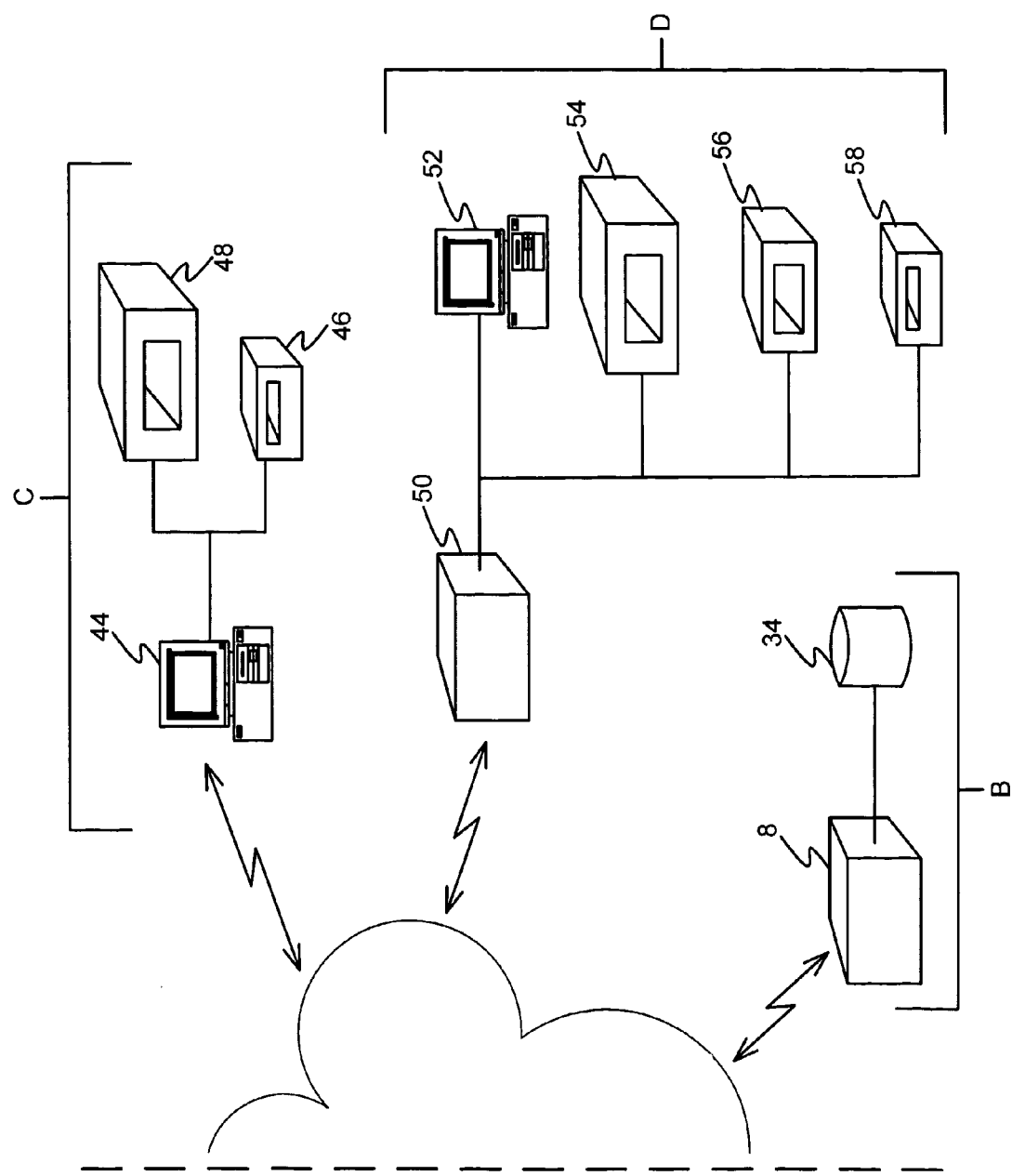

Patient healthcare management system A includes a medicament dispenser 2 which includes an outer housing which takes a refill 4, containing medicament, which is inserted into a receiving inlet 5 of the dispenser and securely fastened therein. The refill 4 is removable therefrom once the refill is empty, or near to empty, to be replaced by a further refill. The dispenser includes an alphanumeric display 28 for the display of functional data and one or more man machine interface elements, for example buttons 30, for the control of the functions of the dispenser by the patient.

The dispenser 2 is adapted for insertion, in a drop-in fashion, into a docking station 6 for the transfer of data between the dispenser 2 and a service provider network server 8, and for the recharging of a battery and/or charge capacitors providing electrical power in the dispenser, in particular its various functions to be described in further detail below. The docking station includes an electricity mains supply cable 9 and, internally, a voltage transformer for the supply of power at a required low voltage. In case of mains supply failure or unavailability the docking station may further include a back-up battery, which may be rechargeable or non-rechargable.

The docking station 6 also includes a communications module 10 for communicating with a corresponding communications module 12 on a network interface device 14. The network interface device 14 includes a network interface module 16 for access to a public data communications network 18, such as the Internet. Both the docking station and the network interface device 14 may be located in a patient's home. The communications modules 10, 12 preferably communicate via a radio interface protocol, such as the Bluetooth™ radio protocol, thereby allowing the docking station 6 to be located at a selected point in the patient's home, such as a bedroom or bathroom, remote from the network interface device 14. The network interface module 16 may comprise one or more of a PSTN modem, a DSL modem, a cable modem, a wireless radio network modem. The network interface device may itself take the form of an appropriately configured personal computer workstation, digital television set top box, home communications hub, etc.

Figure 2:
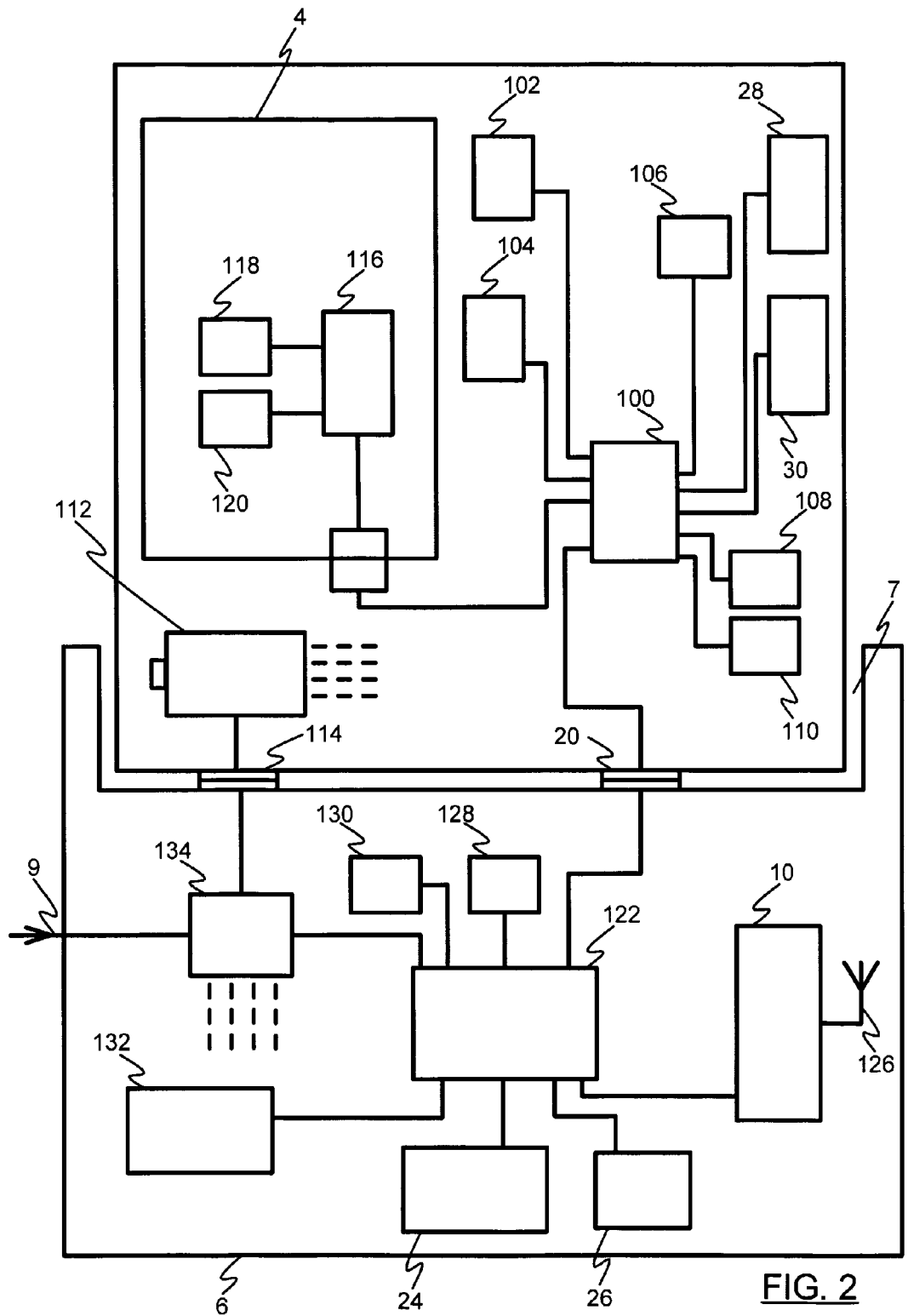
FIG. 2 is a schematic illustration of patient apparatus in accordance with an embodiment of the invention.

FIG. 2 schematically illustrates the electronic components of the medicament dispenser 2, refill 4 and docking station 6 in greater detail.

The dispenser 2 includes a data processor, for example an integrated circuit chip containing a microprocessor 100 and non-volatile memory, in the form of for example ROM 108 and EEPROM 110. Some parts of the memory are reserved for writing to during the manufacture of the dispenser and are, following manufacture, read-only or effectively read-only by virtue of being protected by a secret authentication code, preferably known only by the manufacturer. These read-only parts include a memory portions storing one or more of a unique identifier for the dispenser, a random or pseudo-random password related thereto, one or more type codes for the one or more different types of medicament the dispenser is intended to be used with, a usage lifetime indicator in the form of an expiry date and/or a prescribed maximum number of usages for the dispenser, manufacturing compliance check data and manufacturer details. Other parts are writable and are preferably protected, requiring a predetermined authentication step to have been performed before being capable of being written to, or rewritten. A first set of one or more records are intended to be written initially during dispensing of the dispenser, including one or more of a service provider identifier and/or service provider network address, activation flag, details of an initially prescribed treatment regimen, a version number thereof, and patient name and other patient details. A second set of one or more records are intended to be written initially to by the docking station 6, including records indicating a variation from the original treatment regimen, a version number thereof, and a deactivation flag. A third set of one or more records are intended to be written initially to by the dispenser during use, including compliance monitoring data records indicating when medicament has been taken by the patient and what amount thereof. Some further parts of the memory, containing secret data and/or algorithms, are not externally readable and only for internal use by the microprocessor in performing authentication and encryption procedures. The dispenser 2 comprises external electrical contacts 20, corresponding to contacts in the docking station, for writing data to and reading data from the dispenser, and for charging the battery and/or capacitors of the dispenser.

The refill 4 includes a data processor, for example an integrated circuit chip containing a microprocessor 116 and non-volatile memory, in the form of for example ROM 118 and EEPROM 120. Some parts of the memory are reserved for writing to during the manufacture of the refill and are, following manufacture, read-only or effectively read-only by virtue of being protected by a secret authentication code, preferably known only by the manufacturer. These read-only parts include one or more memory portions storing one or more of a unique identifier for the refill, a type code for the stored medicament, a medicament name, an expiry date, an original dosage amount, manufacturing compliance check data and manufacturer details. Other parts are writable and are preferably protected, requiring a predetermined authentication step to have been performed before being capable of being written to, or rewritten. A first set of one or more records are intended to be written initially during dispensing of the refill, including one or more of an activation flag, details of a prescribed treatment regimen, a version number thereof, and patient name and other patient details. A second set of one or more records are intended to be written initially to by the medicament dispenser, including one or more records indicating a current dosage amount remaining. Some further parts of the memory, containing secret data and/or algorithms, are not externally readable and only for internal use by the microprocessor in performing authentication procedures. The refill 4 comprises external electrical contacts 22, corresponding to contacts in the dispenser 2, for writing data to and reading data from the refill.

The docking station 6 includes a data processor in the form of for example an integrated circuit chip containing a microprocessor 122 and non-volatile memory, in the form of for example ROM 128 and EEPROM 130. Some parts of the memory are reserved for writing to during the manufacture of the docking station and are, following manufacture, read-only or effectively read-only by virtue of being protected by a secret authentication code, preferably known only by the manufacturer. These read-only parts include one or more memory portions storing one or more of a unique identifier for the docking station, manufacturing compliance check data and manufacturer details. Other parts are subsequently writable. A first set of one or more records are intended to be written to from the dispenser when the dispenser 2 is docked with the docking station, including a medicament name, a current remaining dosage amount, details of a current treatment regimen and patient name and other patient details. These first records contain data to be displayed on a screen 24. Screen 24 is larger than display 28, and is capable of displaying bitmap images, for example logos, still and video pictures, etc, as well as alphanumeric text, responsive to user interaction via an MMI such as buttons 26. A second set of one or more records are intended to store message data received from service provider network server 8, including one or more records for storing data for messages to be shown on screen 24. A third set of one or more records are for storing control messages to be transmitted to dispenser 2, such as control messages for performing authentication and control messages indicating a variation in treatment regimen, indicating a current dosage amount remaining. A fourth set of records are for storing data for transmission to network server 8, including compliance monitoring data received from dispenser 2, and self-test health check data, and self-test health status data records, containing data such as peak flow rate data in the case of a respiratory inhaler or blood glucose level data in the case of an insulin dispenser, which is recorded by a sensor 132 in, or associated with, the docking station. In an alternative, the self-test health check data may be replaced by patient self-assessment data, wherein the patient inputs, via MMI 26, a self-assessed health condition indicator, for example a figure from 1 to 10, indicative of how the patient feels. The patient may also append the data with text to record additional data relating to their state of health. The self-test health check data, condition indicator data and other data are automatically date stamped for subsequent analysis by network server 8 and presentation, for example via a patient-specific Web site page, via charts and other assessment tools.

Dispenser display 28, for example an LCD screen, is for displaying information to the patient including the name of the medicament contained in an inserted refill, a current dose remaining, a current time, etc. Reminder messages may also be displayed thereon to indicate when a dose of medicament is due to be taken, in accordance with the current treatment regimen. Such a reminder message may accompanied by a timed alarm indication, given for example by an audible (e.g. tone), kinematic (e.g. vibration) and/or visual (e.g. LED) signal generator. Patients may control display menu and functions by means of a user interface, such as buttons 30. When administering medicine, patient opens outlet 32 and presses a button 30 to initiate the dispensing of a dose, or multiple doses, of medicament. The amount dispensed is controlled by dispenser 2 in accordance with a current treatment regimen stored in the memory of the dispenser 2 and/or the refill 4, along with the current date/time and/or stage of treatment.

Dispenser 2 further comprises a dispensing actuator 102, for the automated dispensing of a dose, or multiple doses of medicament. In one embodiment, the medicament is held in refill 4 in powder, liquid and/or gaseous form and a dispensing actuator is adapted to meter out a required dose from refill 4. In another embodiment, refill 4 contains medicament in the form of elements containing discrete amounts of medicament, for example tablets, capsules, powder compartments, etc. and dispensing actuator is adapted to automatically dispense one or more discrete doses of medicament. Dispensing may be initiated by the patient, for example by means of MMI 30. Dispenser 2 further comprises dispensing sensor 104, for sensing the act of dispensing and recording, as monitoring data, the amount, time and date when dispensing occurs. Clock 106 is used for time monitoring and recordal in the dispenser electronic system.

Data interface 22, consisting of two sets of corresponding electrical contacts, is used for the transfer of data between the refill 4 and the dispenser 2. In an alternative embodiment, the interface consists of a contactless radio interface between a passive tag in the refill and an active reader in the dispenser. Data interface 114, consisting of two sets of corresponding electrical contacts, is used for the transfer of data between the docking station 6 and the dispenser 2. In an alternative embodiment, the interface consists of a contactless radio interface, for example a Bluetooth™ radio interface which is operable when dispenser is placed in the proximity of the docking station 6. Power interface 114 consists of two sets of corresponding electrical contacts for the transfer of electrical power between docking station power transformer 134, supplied by mains power source connection 9, and rechargeable battery 112 in the dispenser 2, which acts as a power source for all electronic components in the dispenser 2 and the refill 4. Transformer 134 acts as a power source for all electronic components in the docking station 6. Docking station 6 may also include a rechargeable back-up battery in case of mains power failure.

Docking station 6 includes a data processing system including a microprocessor 122, non-volatile memory in the form of ROM 128 and EEPROM 130, display 24, man machine interface elements 26, radio interface module 10, including radio antenna 126, a mains power source connection 9, and self-test module 132. Self-test module 132 includes a patient health sensor, such as a blood glucose level sensor, peak flow sensor, etc, and may be detachably connectable to the docking station. In an alternative embodiment, self-test module 132 is included in dispenser 2, or may be detachably connectable to the dispenser 2.

Service provider network server 8 is connected to patient record database 34, which stores long-term patient health records to be used by the health system for the treatment of patients under its care. These records store historical patient health and treatment data, including prescription data, treatment regimen compliance data, and health check status data. Service provider network server includes analysis and reporting functions for operating on data contained in the patient health records and for transmitting messages and reports to other healthcare management systems including patient healthcare management systems, physicians' data management systems and pharmacy data management systems.

Manufacturer data management system E includes a manufacturing system server 36, a data writing terminal 38 for writing data to a dispenser 40 during manufacture, and a data writing terminal 40 for writing data to refill 4 during manufacture.

During manufacture, the dispenser memory 108, 110 is written to contain permanent data in the form of one or more of a unique identifier for the dispenser, a random or pseudo-random password, one or more type codes for the one or more different types of medicament the dispenser is intended to be used with, a usage lifetime indicator in the form of an expiry date and/or a maximum number of usages for the dispenser, a geographical region name and/or code, manufacturing compliance check data and manufacturer details. The dispenser memory is also written to with secret data and/or algorithms, which are not externally readable and only for internal use by the dispenser microprocessor in performing authentication and encryption procedures. This secret data includes a secret authentication key, which may be of a shared secret type of a private key of a public/private key combination. The data may also include a public key for one or more service providers, or a trusted third party providing service provider public key details, to authenticate and/or decrypt control messages received from service provider network server 8, which are encrypted and/or digitally signed by the server 8 using its private key and/or the appropriate shared secret key before transmission. The data may also include a public key for one or more manufacturers, or a trusted third party providing manufacturer public key details, to authenticate and/or decrypt data received from refill 4, which are encrypted and/or digitally signed by the manufacturer or on the refill before transmission. Following manufacture, the data written to the dispenser memory, including in particular the unique identifier and the corresponding password and/or shared secret key and/or public key, are transmitted in a secure fashion to service provider network server 8 and stored therein awaiting dispensing of the dispenser 2 to occur. The dispensers are batched and distributed in batches to pharmacies for subsequent dispensing to patients.

During manufacture, the refill memory 118, 120 is written to contain permanent data in the form of one or more of a unique identifier for the refill, a type code for the stored medicament, a medicament name, an expiry date, an original dosage amount, a geographical region name and/or code, manufacturing compliance check data and manufacturer details. The permanent data also includes a digital signature, generated by manufacturer using a secret authenticating key, of the unique identifier and/or other data, which is added to the refill memory. The refill memory may also be written to with secret data and/or algorithms, which are not externally readable and only for internal use by the refill microprocessor in performing authentication procedures. This secret data may include a secret authentication key, which may be of a shared secret type of a private key of a public/private key combination. The data may also, or alternatively, include a public key for the service provider, to authenticate and/or decrypt control messages received from service provider network server 8, which are encrypted and/or digitally signed by the server 8 using its private key and/or the appropriate shared secret key before transmission. Following manufacture, the data written to the refill memory, including in particular the unique identifier and the corresponding digital signature, shared secret key and/or public key, are transmitted in a secure fashion to service provider network server 8 and stored therein awaiting dispensing of the refill 4 to occur. The refills are batched and distributed in batches to pharmacies for subsequent dispensing to patients.

Patient system A also contains a smart card 42 for identifying the patient and storing patient healthcare details, which preferably are replicated in patient record database 34, including general health data, prescription data, allergy data, etc. Smart card 42 includes electrical contacts 43 whereby a smart card reader/writer accesses data records held on the smart card.

Physician data management system C includes a workstation personal computer 44, a smart card reader/writer 46 and a dispenser reader/writer 48. The dispenser reader/writer 48 may be a docking station similar to the patient docking station 6. On visiting a physician, a patient preferably carries their smart card 42. The smart card is inserted in reader/writer 46 to allow the physician to access patient data held thereon and/or patient data held in patient record database 34. The data is accessed via workstation 44. Each physician has a personal username and password providing the physician with authority to access such data, which details are verified by network server 8 before such access is granted. Following consultation, the physician may issue a digital prescription, which is written to smart card 42 and/or patient record database 34.

Pharmacy data management system D includes a server 50, a workstation personal computer 52, a dispenser reader/writer 54, a refill reader/writer 56 and a smart card reader/writer 58. The dispenser reader/writer 54 may be a docking station similar to the patient docking station 6.

When a patient visits the pharmacy to obtain supplies, the patient carries their smart card 42, which is inserted in smart card reader 58 in order to identify the patient and the corresponding prescription. The patient data is accessed via workstation 52. Each pharmacist has a personal username and password providing the pharmacist with authority to access such data, which details are verified by network server 8 before such access is granted. The patient identity is transmitted to network server 8 in order to access and/or the prescription data. The patient's data record indicates whether the patient currently holds a dispenser appropriate for the prescribed medicament. If not, as in the case of a newly diagnosed patient, the network server instructs pharmacist system to dispense a new dispenser 2.

In order to dispense a new dispenser 2, the pharmacist retrieves the appropriate dispenser from the pharmacy stores and inserts the dispenser into dispenser reader/writer 54. The reader/writer 54 reads the dispenser's unique identity and transmits same to network server 8. FIG. 3 shows a look-up table held database in 34, associating each unique dispenser ID, and the associated data fields, corresponding to the original data held in the dispenser memory, provided by manufacturer (illustrated as Field #1 etc.) with a patient ID following dispensing thereof. The reader/writer is then used to write data received from network server 8, containing one or more of a service provider identifier and/or service provider network address, activation message, details of an initially prescribed treatment regimen, a version number thereof, patient ID and name and other patient details, and a geographical region code, to the dispenser memory. The written data is preferably encrypted and/or signed by the network server 8, thereby indicating to the dispenser that a pharmacist having the necessary authority is performing the dispensing operation. Once activated, the dispenser 2 is ready for use with an appropriate refill 4.

In order to dispense a new refill 4, the pharmacist retrieves the appropriate refill from the pharmacy stores and inserts the dispenser into dispenser reader/writer 54. The reader/writer 54 reads the refill's unique identity and transmits same to network server 8. FIG. 2 shows a look-up table held database in 34, associating each unique refill ID, and the associated data fields, corresponding to those originally held in the refill memory, provided by manufacturer (illustrated as Field #1 etc.) with a patient ID following dispensing thereof. The reader/writer is then used to write data provided by network server 8, containing one or more of an activation message, details of a prescribed treatment regimen, a version number thereof, and patient ID, name and other patient details, and a geographical region code, to the refill memory. The written data is preferably encrypted and/or signed by the network server 8, thereby indicating to the refill that a pharmacist having the necessary authority is performing the dispensing operation. Once activated, the refill 4 is ready for use with an appropriate dispenser 2.

In one embodiment, the pharmacy procedures include reading the data stored on the dispenser and/or refill prior to dispensing, and modifying the dispensing operation accordingly, either in the pharmacy system alone or in combination with the network server system. For example, the pharmacy may be prevented from dispensing a device having a geographical region name and/or code which does not correspond for refills and dispensers, or if the location of the pharmacy does not correspond therewith.

The look-up tables shown in FIGS. 3 and 4 are used for the correct identification of a patient by means of the corresponding dispenser and/or refill ID's. When data is transferred from a dispenser 2 and/or a refill 4 to network server 8, the data includes the device ID and/or the refill ID. Thereby, the patient is identified without requiring the patient to input username and/or password details each time data is sent to the network server 8. Furthermore, the associated authentication procedures may be performed by means of the devices themselves, rather than the patient having to identify and carry out authentication each time sensitive data is transferred. The corresponding shared authentication data, such as shared secret keys, held on both the devices and in the device-related parameter fields illustrated in FIGS. 3 and 4, may be uniquely correlated by means of the look-up tables to the identity of the patient to whom the device was prescribed. In an alternative embodiment, the unique patient ID is written at the pharmacist onto the dispenser and/or refill during dispensing, and the patient ID is sent with any data sent from dispenser to network server 8. However, in this case a device ID, which may be unique amongst all devices, or unique only in combination with the patient ID, is preferably also sent to allow the identification of the device currently being used by the patient at the network server 8. In any case, the data transmitted to network server 8 contains a unique identity, preferably device ID, whereby the corresponding patient record may be accessed.

Figure 5:
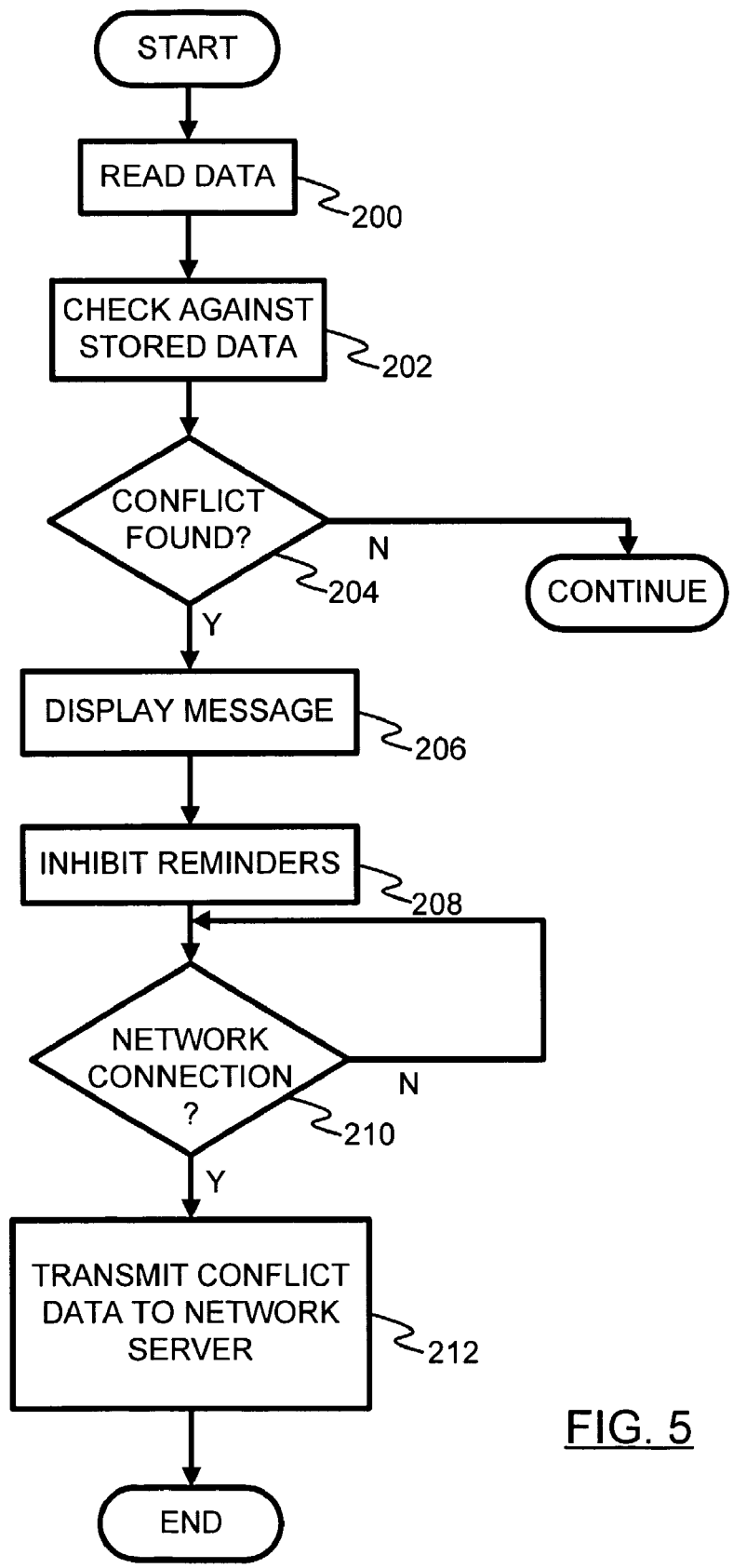
FIGS. 5 to 8 are flow diagrams illustrating procedures carried out in accordance with embodiments of the invention.

FIG. 5 is a flow diagram illustrating procedures carried out in the dispenser 2 on insertion of a refill 4. On insertion of the pharmacy-dispensed refill 4 into the pharmacy-dispensed dispenser 2, the dispenser reads all available data held in refill memory, step 200. The dispenser then checks that no conflicts exist between the data read and that stored in its memory, steps 202 and 204, including ensuring that the refill has a matching patient ID, acceptable medicament type code, acceptable geographical region code, etc. Furthermore, dispenser 2 checks that the any digital signature accompanying the parameter data held in refill is correct. This check is carried out, in one embodiment, by reading the appropriate signature and decrypting it with the public key of the network server 8 to ensure that it corresponds with the original data, for example the unique identity of the refill 4, to which the signature is attached. In other embodiments, other cryptographic methods are used to check the authenticity of the refill by means of public/private key or shared secret key encryption/decryption methods. If a conflict is found, a conflict indicator signal is generated. If no conflict is found, the dispenser checks if there are any updates to be received from the refill. For example, the refill may contain a more recent treatment regimen, which may be detected by means of a later version number. If an update is detected, it is first authenticated, by checking the accompanying digital signature, before updating the appropriate parameters in its memory. If the update authentication fails, a conflict indicator signal is generated. Otherwise, following any update, the dispenser 2 begins a normal treatment regimen in accordance with data held on the dispenser and/or the refill 4. If a conflict indicator signal is generated, the dispenser display 28 is activated to show an appropriate error message, for example "Refill not authorised: see pharmacist", step 206. The dispenser 2 also inhibits any reminder programme which would otherwise have been followed, step 208. On generation of the conflict indicator signal, the dispenser may, in one embodiment, write a deactivation flag in the dispenser or refill memory to prevent the refill and/or the dispenser being used, at least until the conflict is resolved by means of an update message received from server 8. Alternatively, the dispenser may still be used in manual override mode to dispense medicament from the refill, even though the data management functions are not made available. Further alternatively, the dispenser may continue to operate normally but store the conflict data to transmit same to network server 8 when the dispenser is next docked. The action taken by dispenser may depend upon the nature of the conflict found. For example, if the refill contains the wrong type of medicine, the refill may be fully deactivated. On the other hand, if the refill was dispensed to a different patient, but contains the correct type of medicament, the dispenser may be used as normal, with the conflict data being sent to network server 8 to be written to the patient record in order that a healthcare professional, such as the physician or pharmacist, may be made aware of the conflict when the patient record is next accessed.

The dispenser then senses whether a docking connection is made to docking port 6, for example by means of a data read signal being received from docking port 6, at which point an message indicating the detected conflict is sent, via docking station 6, to network server 8, steps 210 and 212. Network server 8 may used the conflict data for monitoring purposes, and inform the appropriate healthcare professional as and when required of the detected conflict. For example, when patient next visits a pharmacist, the pharmacist will be able to access, via the patient record, the conflict data and indicated the nature of the problem to the patient. If the conflict is an internal conflict caused by an error in the network server system 8, the conflict may be resolved and updates may be sent to all other affected dispensers to avoid the conflict occurring unnecessarily elsewhere. Preferably, the dispenser may still be used in manual override mode to dispense medicament from the refill, even thought the data management functions are not made available.

In any case, when a conflict is found, conflict data indicating the cause of the conflict, e.g. both the data derived from the refill and the corresponding, incompatible, data held on dispenser, is transmitted to network server 8. Network server 8 analyses the nature of the conflict and can take remedial action, such as writing corresponding data to patient record for perusal by a healthcare professional having access to the system, transmitting informational messages to the patient via the patient docking station, and/or transmitting update messages to the dispenser via the docking stations to resolve the conflict by updating one or more fields of the dispenser memory as appropriate.

If no conflict is found, the unique identity of the refill and/or other details held on the refill are written to a record in the dispenser memory for transfer, via docking station 6, to the network server 8 when the dispenser is next docked. Such data, derived from the refill, is then stored in the appropriate patient record by the network server 8, to provide a medication history, including details of the refill container used, for the patient. Furthermore, in an alternative embodiment, any conflict checks are carried out by network server. In this embodiment, the current refill ID and device ID are preferably transmitted to network server 8, and the corresponding parameter data, held in the lookup tables illustrated in FIGS. 3 and 4, is analysed by network server 8 to determine whether a conflict exists. Alternatively, one or more of the other parameter data items held in the dispenser memory and/or the refill memory may be transmitted to network server 8. If a conflict is found, network server 8 analyses the nature of the conflict and can take remedial action, such as writing corresponding data to patient record for perusal by a healthcare professional having access to the system, transmitting informational messages to the patient via the patient docking station, and/or transmitting update messages to the dispenser via the docking stations to alter the functioning of the dispenser, to disable the dispenser until a new refill has been inserted, and/or to resolve the conflict by updating one or more of the previously incompatible fields of the dispenser memory as appropriate.

Figure 6:
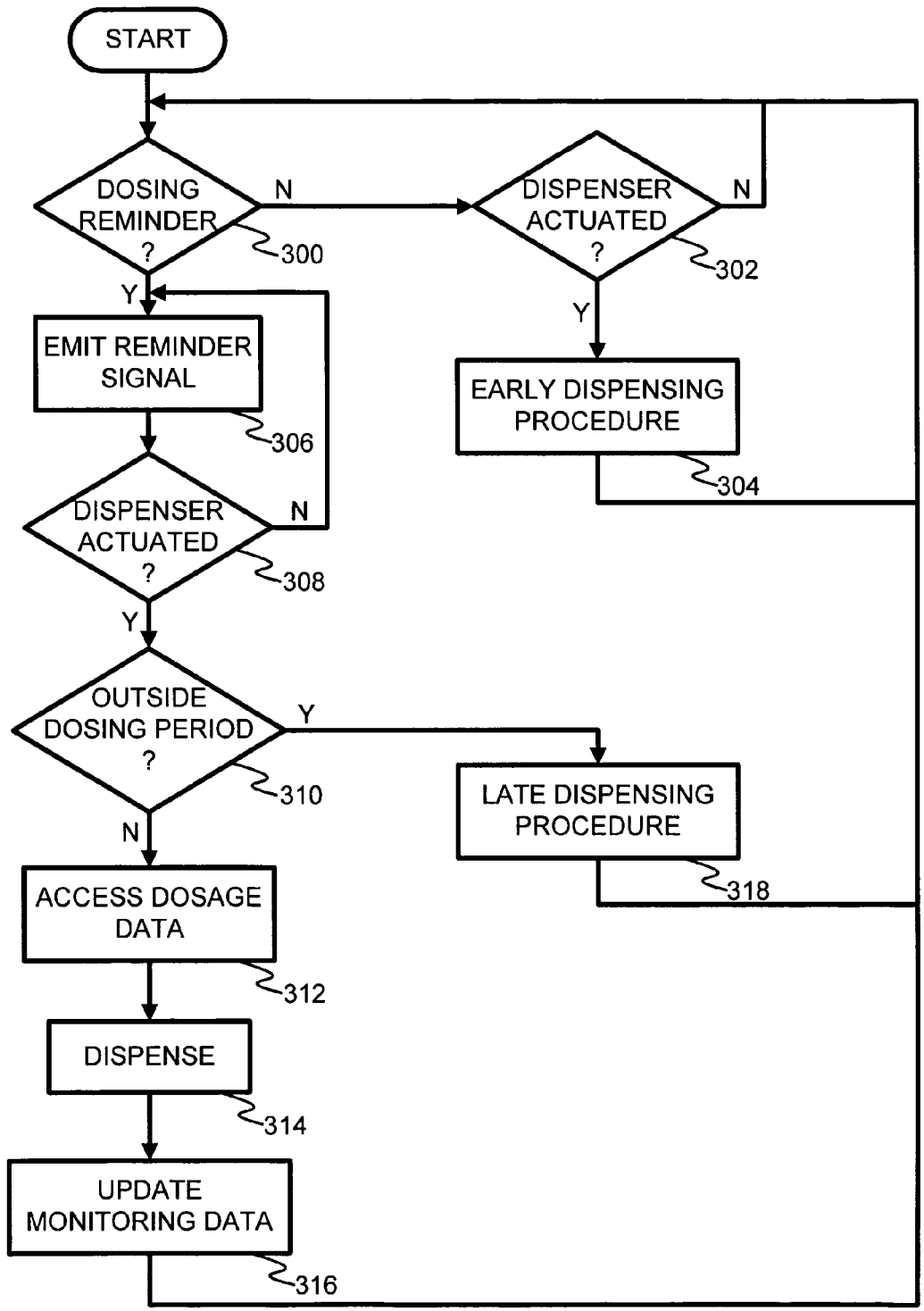

FIG. 6 illustrates a treatment procedure followed by dispenser 2 when loaded with a correct refill 4. The dispenser holds treatment regimen data from which it is determined when a medicament dose is due to be taken by the patient, step 300. A period is defined when the dose is defined to be correctly taken, by means of a start date/time and an end/date time, which may be defined relative to a last taken medication or in accordance with an absolute timing policy. If the patient activates the dispenser prior to the start date/time, step 302, the dispenser acts in accordance with an early dispensing procedure, step 304, which is different to the normal dispensing procedure. This may be to at least initially inhibit dispensing and display a message to the patient indicating that it is too early to take another dose. An option may at this stage be given to allow the patient to confirm that a dose is required, in response to which the dispenser conducts dispensing as required. Alternatively, dispenser may initially dispense the dose at the requested time, and update the subsequent reminder schedule to cancel the upcoming reminder and bring forward the subsequent reminders.

When a dosing reminder is due, the dispenser 2 emits a dosing reminder signal, step 306. The signal may be an audio, visual and/or kinematic signal, and may vary over time depending on whether dosing is carried out by the patient, for example to increase in intensity over time. When patient actuates the dispenser to dispense a dose of medicament, step 310, the dispenser determines whether the dispensing operation is later than the predefined end date/time for the normal dosing period, step 310. If so, a late dispensing procedure, different to a normal dispensing procedure, is carried out, step 318. This may consist of indicating to the patient that the dose is being taken late and adjusting the subsequent reminder schedule accordingly, to delay subsequent reminders in accordance with the delay. If within the normal dosing period, the normal dosage data is accessed, step 312, and the appropriate dosage is dispensed, step 314. Following all dispensing procedures, although only shown in relation to normal dispensing procedure, the monitoring data held in dispenser, subsequently to be sent to network server 8, is updated to store details of the latest dispensing event, including date/time, amount dispensed, and any other pertinent data such as patient health data (e.g. peak flow rate) detected during the dispensing operation.

Figure 7:
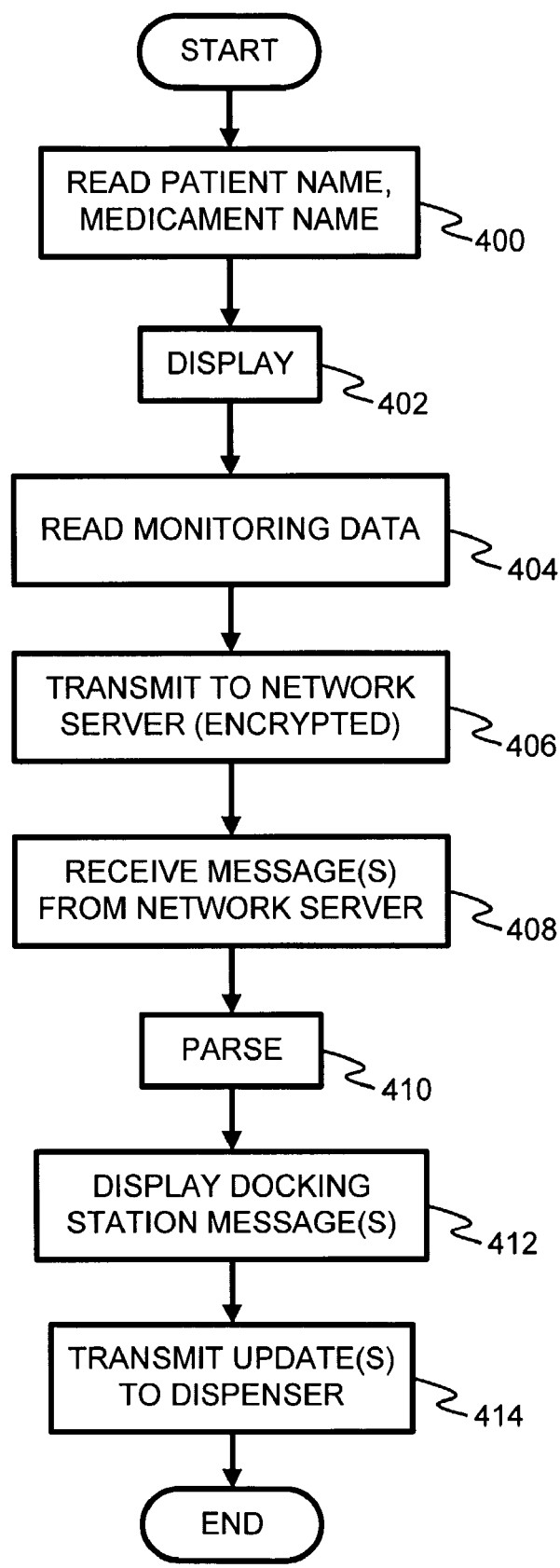

FIG. 7 illustrates a procedure carried out by docking station 6 when a dispenser is docked therein. Note that in this preferred embodiment, the docking station 6 may be used with multiple different dispensers, including multiple dispensers owned by the same patient and/or multiple dispensers owned by different patients.

On receiving a dispenser 2, the docking station 6 first reads the patient name and medicament name, along with other pertinent data such as number of doses remaining, etc., and displays these details to the patient, steps 400, 402, via display 24. The patient may scroll through the relevant data held on dispenser by means of an MMI interaction. Next, the docking station reads other stored data from the dispenser, including the dispenser identity, the refill identity, any conflict data resulting from a conflict check conducted by dispenser 2, and dispensing monitoring data stored when the patient has dispensed medication from the dispenser 2. This stored data may be provided by the dispenser in encrypted form, for example encrypted using its stored secret key, for transmission by the docking station in encrypted form, step 406, and decryption by the network server 8 with reference to the corresponding decryption key held in the details held for the identified dispenser. Furthermore, authentication data, in the form of a digital signature produced by the dispenser 2 and/or the refill 4, may also be transmitted for checking by network server. The docking station may form a suitable data connection, for example a TCP/IP socket connection, to the network server 8. The connection between the docking station 6 and the network server 8 may in any case be arranged to be secure, for example via secure socket layer (SSL) interactions. The data sent by docking station is analysed at the network server 8 and one or more response messages are generated and sent to be received by docking station, step 408. These messages may be structured as extensible markup language (XML) documents. The responses preferably comprise data to be displayed to user via the display screen 24 of the docking station, and update data to be passed by docking station. Docking station 6 parses the response data, step 410, displays the display content, step 412, and transmits any update messages to the dispenser 2, step 414. The update messages are preferably encrypted by network server 8 using the corresponding encryption key, for example the dispenser's shared secret key or the public key of the dispenser, and/or contain a further authentication element, such as a digital signature authenticating the data as having been generated by, or with the authority of network server 8.

Figure 8:
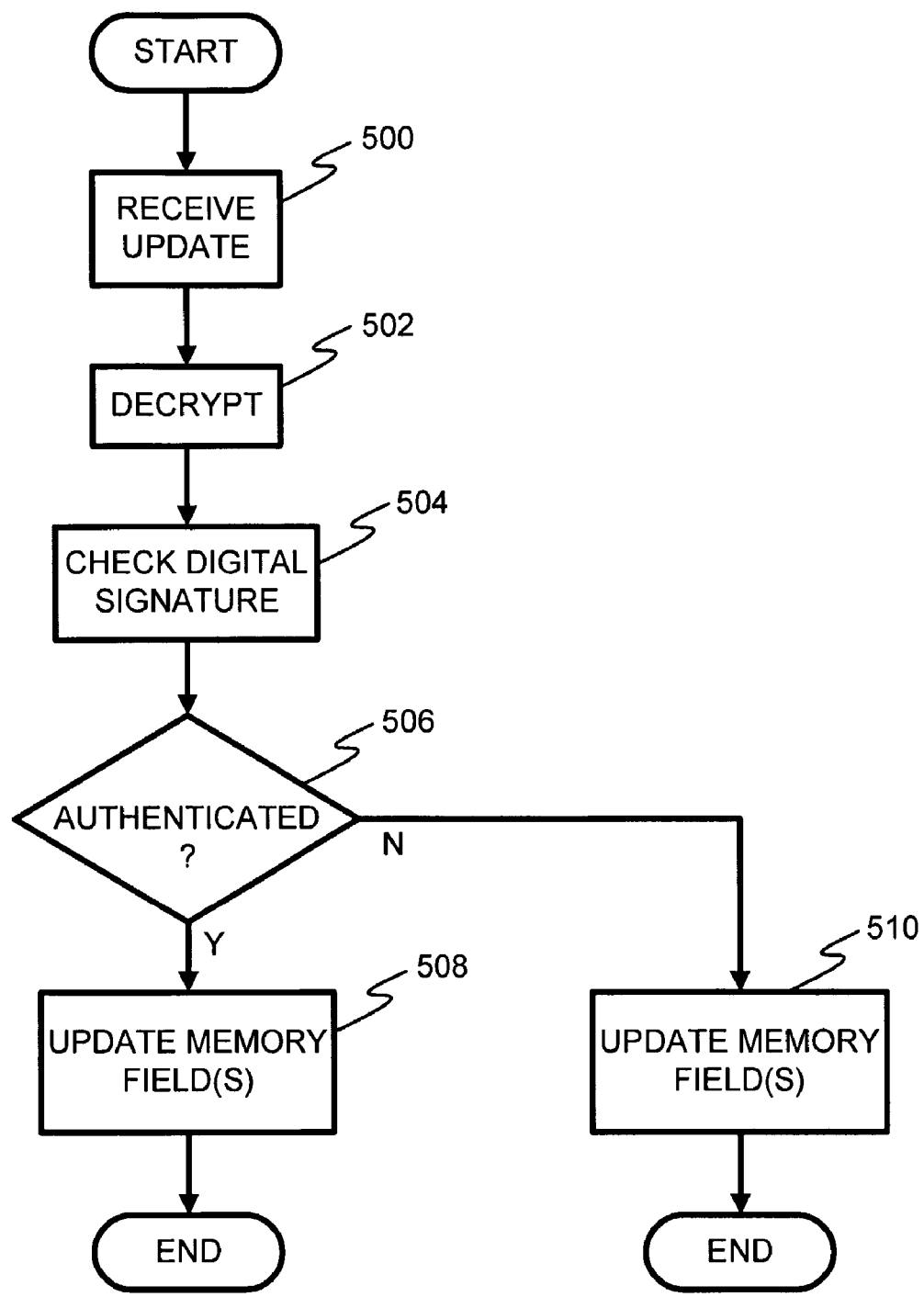

FIG. 8 illustrates steps taken by dispenser 8 on receipt of an update message via docking station 6, step 500. Initially, the dispenser 2 conducts decryption of the data using a secret key stored in the dispenser memory, step 502. Next, the dispenser checks the accompanying digital signature, step 502. If either of these steps fails, the update message cannot be authenticated, step 506 by dispenser 2 and an error message is displayed, step 510. An error message may also be sent to network server 8, to allow a further, corrected, update to be sent. If the update is authenticated by the dispenser, step 506, the corresponding data fields are updated in the dispenser memory and/or the refill memory, step 508. It is to be noted that any one or more of the writable fields of the dispenser and/or the refill, such as any of those previously mentioned, may be updated in this way.

If the dispenser 2 and/or the refill 4 fails to authenticate to network server 8, the network server can send an appropriate message to the docking station, such as "Authentication failed: please visit pharmacy".

In a subsequent physician visit, if the patient has brought their dispenser 2, and the dispenser is inserted into reader/writer 48 in order for the most recent compliance and health status data to be downloaded to network server 8. The dispenser's unique identity is transmitted to network server 8, along with authentication data in the form of the corresponding password and/or, if stronger authentication is required, an encrypted response to a challenge message sent by the server 8, which response is verified by server 8 in order to validate the dispenser identity. The corresponding patient identity is looked up by network server in order to access the correct patient record.

Not only does physician have access to patient data, but also the analysis and reporting functions provided by network server 8 following the period of patient compliance and health monitoring provided by dispenser 2. Following consultation with the network server functions and the patient, the physician may vary the treatment regimen, by input to workstation 44 which results in an update procedure whereby network server 8 transmits data to be written to the dispenser by reader/writer 48. The transmitted data is encrypted and/or digitally signed by the network server, using the appropriate secret and/or private key for the dispenser 2. On receipt, the dispenser decrypts and/or authenticates the control data and, if authentication is successful, updates its records accordingly. The physician may also prescribe more or a new medicament, in which case a digital prescription is written to smart card 42 and/or to patient record database 46.

If on docking with docking station 6, either the docking station or the network server 8 establishes that the patient is due for another prescription, a message may be displayed to the patient inquiring whether a further prescription should be ordered. If the patient replies in the affirmative, a represcription order placed in the patient record, or is transmitted to a selected pharmacist, and the patient may pick up the appropriate refill by presenting at the pharmacist with their patient smart card 42.

The network server-based system also monitors the lifetimes of dispensers and/or refills. Namely, associated with each of the dispensers and refills, by means of parameter data held against the device identity in the look-up tables illustrated in FIG. 4, is an expiry date for the device, and when the device is due to expire, a suitable message may be sent to a docking station instructing the patient to order the prescription of a new device. On expiry an update message may be sent to the dispenser via the docking station to disable dispensing. The lifetime of the dispenser may be based solely on an expiry date, a usage amount (e.g. maximum number of allowed uses), or both. In any case, such monitoring and messaging is useful in order to inhibit the at least inconvenient failure of any of the devices used by the patient.

In the above-described embodiments, the patient is identified primarily by means of the dispenser and/or the refill which they have been dispensed by a registered pharmacist. Additional identity checks may be carried out by the system. For example, the dispenser 2 or the docking station 6 may include a Biometric sensor such as a fingerprint sensor for positively identifying the patient before any actions based upon the patient identity are carried out.

In different embodiments of the invention, the dispenser is typically shaped to define a cavity within which the refill is receivable. The dispenser and/or refill may be further shaped with grooves, indentations or other shaping or surface details to define a slidingly lockable/releasable relationship between the dispenser and the refill. Accordingly, the dispenser may have a lockable cover which is releasable to expose the cavity within which the refill is held.

FIGS. 9a and 9b show a metered dose inhaler comprising a dispenser in the form of a tubular actuator housing 601 shaped for receipt of an aerosol refill 602. The actuator housing is open at one end and is closed at the other. An outlet 603 leads laterally from the closed end of the housing 601. In the embodiment illustrated, the outlet 603 is in the form of a mouthpiece intended for insertion into the mouth of the patient but it may, if desired, be designed as a nozzle for insertion into the patient's nostril. The aerosol refill 2 has an outlet valve 604 at one end. This valve acts as a release means for release of a measured dose from the aerosol refill. The release means is actuable by inward movement of the valve 4 relative to the aerosol refill 602.

The metered dose inhaler of FIGS. 9a and 9b includes an electronic data management system 610, including all electronic components and electrical connections, and is adapted for docking with a corresponding docking station, as described above in detail, comprised within an extended part 606 of the housing 6. A visual display (not visible) allows for display of information from the electronic data management system 610 to the patient. The electronic data management system connects to a sensor (not visible) for sensing the breathing pattern of the patient and an actuator (not visible) for actuating the release of aerosol from the refill 2.

A data module in the form of a chip 620 is mounted on the side of the aerosol refill 602. Corresponding read/write contacts 630 for the chip 620 are moulded into the internal surface of the dispenser housing 601. In an alternative embodiment the data module 620 comprises a radiofrequency identification tag and the read/write module 630 is capable of reading data therefrom and writing data thereto by the use of interrogating radiofrequency energy. In another embodiment the data module 620 comprises a magnetic label and the read/write module 30 is capable of reading data therefrom and writing data thereto by the use of interrogating magnetic field energy.

FIG. 10 shows a schematic representation of a breath-operable medicament dispensing system, which is an embodiment of the system shown in FIGS. 9a and 9b. The system comprises a metered dose inhaler similar to that shown in FIGS. 9a and 9b, comprising tubular housing 710 having a dispensing outlet 712 in the form of a mouthpiece. Within the housing 710 sits aerosol refill 720 which has a valve dispensing mechanism 722 in the form of a slide valve. Valve stem 724 is supported by valve support 714. Outlet passage 716 is provided in the support 714 to enable passage of dispensed dose to the dispensing outlet 712.

It may be seen that the upper part of the aerosol refill 720 abuts refill seat 730. The refill seat 730 comprises an insulating portion 732 which directly contacts the aerosol refill 720 and an upper conducting portion 734 (e.g. comprised of aluminium). It may also be seen that the valve support 774 connects with conducting valve seat 740. Plural shape memory alloy wires 750a, 750b connect the conducting portion 734 of the refill seat 730 to the conducting valve seat 740. The plural wires 750a, 750b comprise a nickel-titanium alloy which contracts in response to electrical current flow therethrough. It may thus, be appreciated that on passage of electrical current through the plural wires 750a, 750b the refill seat 730 and valve seat 740 will be drawn towards each other as the wires 750a, 750b contract. Actuation of the valve dispensing mechanism 722 and dispensing of medicament dose will thereby result.

Control of electrical current flow to the refill seat 730, valve seat 740 and wires 750a, 750b is achievable using the illustrated circuitry. Refill seat 730 and valve seat 740 connect to actuation circuit 760 which includes a high current power supply 762 (e.g. a voltaic cell or battery of voltaic cells) and a switch 764 in the form of a solid state relay. The solid state relay 764 itself connects with control circuitry including a micro-controller 770 having an independent power supply 772. The micro-controller 770 itself connects with pressure transducer 780 which has an input in the form of a pressure tube 782 located within the dispensing outlet 772 of the inhaler housing 770.

It may be appreciated that current flow to the refill seat 730, valve seat 740 and wires 750a, 750b, and hence actuation of the valve dispensing mechanism may be achievable as follows. The patient inhales through the mouthpiece 772 resulting in a change in pressure within the housing 770 and pressure tube 782. The change in pressure is detected by the pressure transducer 780 which sends a signal to the micro-controller 770. The micro-controller 770, in turn sends a switching signal to the solid state relay 764 which results in closing of the actuation circuit and electrical current flow therethrough. The resulting contraction of the shape memory alloy wires 750a, 750b causes actuation of the valve dispensing mechanism 722 and hence, dispensing of medicament to the inhaling patient.

It may also be seen in FIG. 10 that the micro-controller 770 is connected to a display 774 for display of information to the patient and also with a computer interface 776 for exchange of data therewith. All circuitry and components thereof including the power supplies 762, 772 and display 774 may be arranged to be present on the housing 770 such that the system is in the form of a discrete, hand-held device.

Figure 11:
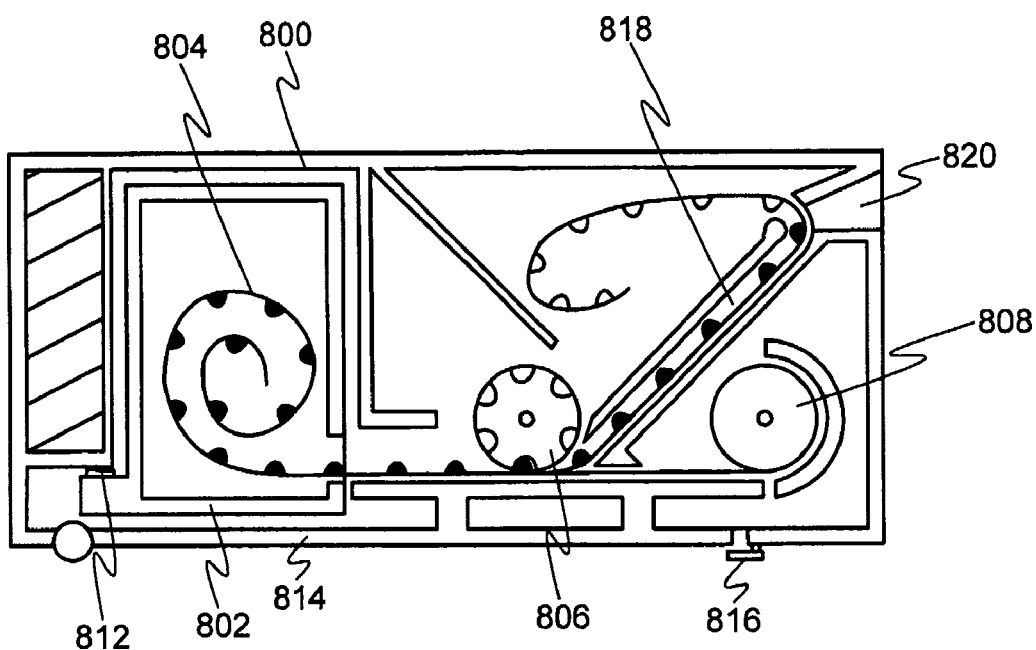

FIG. 11 shows a medicament dispenser 800 containing a refill cartridge 802 in accord with a further embodiment of the present invention. The medicament refill cartridge 802 comprises a flexible strip 804 defining a plurality of pockets each of which contains a discrete dose of medicament. The doses may be in the form of tablets, capsules, doses of powder which can be inhaled, etc.

The strip 804 comprises a base sheet in which blisters are formed to define the pockets and a lid sheet which is hermetically sealed to the base sheet except in the region of the blisters in such a manner that the lid sheet and the base sheet can be peeled apart. The lid and base sheets are each preferably formed of a plastics/aluminium laminate and are preferably adhered to one another by heat sealing.

FIG. 11 shows the internal mechanism of medicament dispenser 800 in the situation where the majority of the pockets of the refill strip 804 are still filled with medicament. The internal mechanism comprises an index wheel 806 and a lid-winding spool 808 for winding the used portion of the lid sheet. The index wheel 806 has a plurality of recesses extending parallel with the axis of the wheel. The recesses are spaced at a pitch which is equal to the distance between the centre lines of adjacent pockets in the refill strip 804.

The refill 802 includes an internal area for the medicament strip 802 to be coiled in prior to use of the doses contained inside it. The dispenser comprises an area where the used base and lid of the medicament carrier strip 804 is collected. After complete usage, the used base may be rewound back into refill automatically prior to removal of the refill.

The dispensing system 800, 802, includes an electronic data management system 810, including all electronic components and electrical connections, as described above in detail, and is adapted for docking with a corresponding docking station as described in detail above.

The refill 802 includes a data module 812 in the form of a chip, as described above, which interfaces with the data management system 810 when the refill 802 is inserted in the dispenser 800, via a hinged insertion door 814, which is secured in place by means of a catch 816. On insertion of the refill, the lid sheet is wrapped around spool 808 and the base sheet, containing the pockets of medicament, is inserted in transport passage 818 of the dispenser. Spool 808 and/or index wheel 806 are revolved, by means of a motor controlled by data management system 810 a predetermined amount for each dispensing operation. As the dispensing operation occurs, a new dose of medicament is presented at outlet 820 for consumption by the patient.

Medicament dispensers of the present invention are in one aspect suitable for dispensing medicament for the treatment of respiratory disorders such as disorders of the lungs and bronchial tracts including asthma and chronic obstructive pulmonary disorder (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the ftiroate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]-ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); α₄ integrin inhibitors e.g. (2S)-3-[4-({[4-(aminocarbonyl)-1-piperidinyl]carbonyl}oxy)-phenyl]-2-[((2S)-4-methyl-2-{[2-(2-methylphenoxy)acetyl]amino}pentanoyl)-amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an anti-inflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

The medicament dispenser of the present invention in other embodiments comprises a syringe for the delivery of injectable medicament to a patient. Traditional syringes rely on puncturing of the patient's skin by a hollow needle through which the injectable medicament (in solution or suspension form) is delivered to the muscle or tissue of the patient. Recently developed needleless systems for the delivery of injectables employ high velocity injection of particle formulated drugs or vaccine through the skin and into any physically accessible tissue. Other needleless systems employ similar high velocity injection of drug or vaccine coated on to a suitable carrier particle.

It will be understood that the present disclosure is for the purpose of illustration only and the invention extends to modifications, variations and improvements thereto.

In alternative embodiments, there is no docking station situated in the patient home or other environment. However a docking station 6 as described may be provided in a health care provider location, such as in patient clinic, physician's surgery or pharmacist. In this, and other alternative embodiments, the dispenser contains a sealed long-life battery.

In the above embodiments, the service provider authentication and decryption procedures for updates messages are carried out by the dispenser 2. In an alternative embodiment, the authentication and/or decryption is performed by the docking station 6.

In the above embodiments, the refill is filled with medicament at the site of manufacture. In an alternative embodiment, the refill may be filled in pharmacy, and its memory written to with data identifying its contents and expiry date therefore.

In the above embodiments, authentication is performed by means of encryption/decryption and by means of digital signature checking. Other known methods of authentication may also, or alternatively be used. Herein the term digital signature is intended to include digital certificates, which also provide means of authentication.

In the above embodiments, the docking station must first establish a connection with the network server in order for update and display messages to be sent to the patient. Other means of delivery of messages, in particular push messages sent by the server at a time determined by the server, may be sent in other formats, for example by means of cellular telephony SMS messages, and to other devices, such as cellular radio devices.

In this description, and in the following claims, the devices involved in the present invention include a dispenser and a refill. It is to be noted that the dispenser is not limited to a device comprising a medicament outlet; the outlet may be provided on the refill. The dispenser is a device containing elements for the control of a dispensing operation in which medicament, originally contained in the refill, is dispensed.

The invention claimed is:

1. A method of controlling the functioning of a portable medicament dispenser, said portable medicament dispenser being for use with a refill container which is insertable in said medicament dispenser in order to perform dispensing of medicament from said refill container, said method comprising:

(a) providing a memory for storing one or more parameters relating to the functioning of said dispenser;

(b) storing authentication data for authenticating data for controlling a function of said dispenser;
(c) receiving control data for said dispenser;
(d) performing authentication of the control data using said stored authentication data;
(e) in dependence on a result of the authentication, activating one or more parameters in said memory to control functioning of said dispenser in accordance with said control data,
wherein step (c) comprises receiving said control data in a refill container; and
step (d) comprises performing authentication of the control data in said refill container,
and in that following said authentication, said control data is stored on said refill container, such that said control data can be transferred to said memory following insertion of said refill container into said dispenser.

2. A method according to claim 1, wherein the step of authentication comprises checking a code accompanying the control data.

3. A method according to claim 2, wherein said authentication data comprises an encryption key whereby said code is checked.

4. A method according to claim 2, wherein said code comprises a digital signature formed by digital signature generation from said control data.

5. A method according to claim 1, wherein the step of authentication comprises decryption of said control data.

6. A method according to claim 5, wherein said authentication data comprises an encryption key whereby said control data is decrypted.

7. A method according to claim 6, wherein said encryption key used for decryption of said control data is a shared secret key.

8. A method according to claim 1, wherein the authentication comprises a cryptographic challenge/response procedure.

9. A method according to claim 1, wherein said step of authentication further comprises performing authentication in said portable medicament dispenser.

10. A method according to claim 1, wherein said portable medicament container is for use with a docking station, and wherein said step of authentication further comprises performing authentication in said docking station for said dispenser.

11. A method according to claim 1, wherein said portable medicament dispenser is for use with a node of a data communications network, and wherein said control data comprises control data received from said network node.

12. A method according to claim 1, wherein said control data comprises data arranged to control a dose count function of said dispenser.

13. A method according to claim 1, wherein said control data comprises data arranged to control a reminder function of said dispenser.

14. A method according to claim 1, wherein said control data comprises data arranged to control a dosage amount during a dispensing operation.

15. A portable medicament dispenser, said portable medicament dispenser comprising a refill container which is insertable in said medicament dispenser in order to perform dispensing from said refill container, said dispenser comprising:

(a) a memory for storing one or more parameters relating to the functioning of said dispenser;
(b) means for storing authentication data for authenticating data for controlling a function of said dispenser;

(c) means for receiving control data for said dispenser;
(d) means for performing authentication of the control data using said stored authentication data;
(e) means for, in dependence on a result of the authentication, activating one or more parameters in said memory to control functioning of said dispenser in accordance with said control data, wherein said means (c) comprises means for receiving said control data in said refill container; and said means (d) comprises means for performing authentication of the control data in said refill container;

and in that said refill container is adapted to store said control data following said authentication, such that said control data can be transferred to said memory following insertion of said refill container into said dispenser.

16. A portable medicament dispenser according to claim 15, wherein said means (d) comprises means for checking a code accompanying the control data.

17. A portable medicament dispenser according to claim 16, wherein said authentication data comprises an encryption key whereby said code can be checked.

18. A portable medicament dispenser according to claim 16, wherein said code comprises a digital signature formed by digital signature generation from said control data.

19. A portable medicament dispenser according to claim 15, wherein said means (d) comprises means for decryption of said control data.

20. A portable medicament dispenser according to claim 19, wherein said authentication data comprises an encryption key whereby said control data can be decrypted.

21. A portable medicament dispenser according to claim 20, wherein said encryption key used for decryption of said control data is a shared secret key.

22. A portable medicament dispenser according to claim 15, wherein said means (d) comprises means for performing a cryptographic challenge/response procedure.

23. A portable medicament dispenser according to claim 15, wherein said dispenser further comprises means for performing authentication in said portable medicament dispenser.

24. A portable medicament dispenser according to claim 15, further including a docking station, and wherein said docking station comprises means for performing authentication in said docking station.

25. A portable medicament dispenser according to claim 15, wherein said portable medicament dispenser is for use with a node of a data communications network, and wherein said control data comprises control data received from said network node.

26. A portable medicament dispenser according to claim 15, wherein said control data comprises data arranged to control a dose count function of said dispenser.

27. A portable medicament dispenser according to claim 15, wherein said control data comprises data arranged to control a reminder function of said dispenser.

28. A portable medicament dispenser according to claim 15, wherein said control data comprises data arranged to control a dosage amount during a dispensing operation.

* * * * *